United States Patent
Mayer

Patent Number: 6,077,278
Date of Patent: Jun. 20, 2000

[54] SUTURE NEEDLE HOLDER

[76] Inventor: Paul W. Mayer, 6290 SW. 92nd St., Miami, Fla. 33156-1866

[21] Appl. No.: 09/154,705

[22] Filed: Sep. 17, 1998

Related U.S. Application Data

[60] Provisional application No. 60/059,165, Sep. 17, 1997, and provisional application No. 60/074,657, Feb. 13, 1998.

[51] Int. Cl.[7] .................................................. A61B 17/04
[52] U.S. Cl. ........................ 606/147; 606/139; 606/148
[58] Field of Search .................................... 606/139, 144, 606/147, 148

[56] References Cited

U.S. PATENT DOCUMENTS

| | | |
|---|---|---|
| 532,306 | 1/1895 | Brown . |
| 1,539,221 | 5/1925 | Tennant . |
| 2,363,334 | 11/1944 | Jones . |
| 4,235,177 | 11/1980 | Arbuckle . |
| 4,597,390 | 7/1986 | Mulhollan et al. . |
| 4,635,638 | 1/1987 | Weintraub et al. . |
| 5,300,082 | 4/1994 | Sharpe et al. ............................ 606/147 |
| 5,376,096 | 12/1994 | Foster . |
| 5,454,819 | 10/1995 | Knoepfler . |
| 5,496,336 | 3/1996 | Cosgrove et al. . |
| 5,573,542 | 11/1996 | Stevens . |
| 5,643,289 | 7/1997 | Sauer . |
| 5,792,151 | 8/1998 | Heck et al. . |

Primary Examiner—Michael Buiz
Assistant Examiner—Julian W. Woo
Attorney, Agent, or Firm—Browdy and Neimark

[57] ABSTRACT

A twirlable suture needle holder is operable by one hand. A palm piece (300) rests against the palm and a finger piece is held between the thumb and fingers. The finger piece has a sleeve (100) and a stylet (200) which slide telescopically to grip and release the needle (N). The finger piece is rotatably relative to the palm piece, and the point at which the needle is grasped is offset from the rotation axis by the radius (R) of the arcuate needle. When the surgeon twirls a grip portion (135) of the sleeve while retracting the sleeve to grip the needle; the body of the needle follows the arcuate path traced out by the needle point moving around the axis. The suturing motion uses only small inner muscles of the forearm and requires no rotation of the wrist.

13 Claims, 4 Drawing Sheets

SUTURE NEEDLE HOLDER

This application claims benefit of Provisional Appln. 60/059,165 filed Sep. 17, 1997 and 60/074,657 filed Feb. 13, 1998.

FIELD OF THE INVENTION

The present invention relates to needle holders, especially for suturing needles.

REVIEW OF THE RELATED TECHNOLOGY

Suturing needles are commonly held by hemostat-type clamps. These devices permit the surgeon to hold a needle firmly at one end, and provide a hand-sized grasping portion at sufficient distance from the clamping end to keep the surgeon's hands out of the suturing area. But their design has no relationship to the art of suturing beyond that.

In such conventional needle holding devices the grasping portion is not shaped to fit the hand, which makes for awkwardness, fatigue, and lack of precision.

Worse, the entire hand must be rotated in order to suture. Suturing needles are curved, generally in an arc of a circle, so that the needle can draw the suture into a surface and then out again. To avoid tearing flesh the surgeon must move the tip of the device in a tiny arc and this can only be accomplished with conventional needle holders by rotating the wrist relative to the elbow: this motion is called pronation or supination, depending on whether the rotation is clockwise or counterclockwise, and is accomplished by muscles (pronator and supinator) which wrap around the forearm so that the wrist rotates relative to the elbow when the muscles contract.

Rotation by supination and pronation has several disadvantages.

First, contracting a large forearm muscle exerts a large force, adapted for gross motions instead of fine. When rotating a device held in the hand, it is very difficult to keep the tip of the device in one place; this is easily demonstrated by holding a pencil tip near a point on a surface and rotating the pencil. It will be found that the tip moves several millimeters during the wrist rotation unless the movement is done very slowly and carefully.

Second, the forearm cannot be stabilized against a support because the pronator and supinator, as they tense and relax, change their firmness and shape. The location of these muscles just under the skin, and their large size, mean that the forearm is jostled by tensing and relaxation of the muscles as they rest against a support.

Third, when the ulna bone of the forearm rests against a support, rotation of the wrist causes the hand to move back an forth with the resting point of the ulna as a fulcrum.

In many delicate operations (such as when suturing small cardiac arteries) it is critical that the surgeon must move her or his hand with great precision and follow the arc of the suture needle exactly. But this is very difficult with conventional needle holders.

Once the suture needle has traversed its path through the flesh then the needle will be released and re-grasped. There should be no erratic movement on releasing the needle; that can tear the flesh. The gripping force on the needle should simply vanish. However, the prior-art hemostat-type clamp cannot accomplish this. To release a suture needle from a hemostat-type clamp, the surgeon must exert simultaneous compression and torque to unhook the ratchet teeth which normally lock hemostat jaws together. Even if the needle holder has no clamping mechanism, there will be some motion of the jaws as the large forearm muscles holding the handles together relax.

Although fine control of a suturing needle is important—a matter of life or death in some operations—conventional needle-holding devices do not provide for fine control. The great force available from the pronator and supinator muscles are not needed in suturing, especially in fine suturing when precision is needed most. The smaller, deeper muscles of the forearm would be better used for suturing, but conventional needle holders ignore this possibility.

In addition, prior-art needle holders are no more adapted to the particular motions needed in suturing than is a pair of pliers.

SUMMARY OF THE INVENTION

Accordingly, the present invention has an object, among others, to overcome deficiencies in the prior art such as noted above.

The invention relates to a suturing needle holder that provides more precise and accurate needle control, greater safety, and less fatigue. The invention avoids pronation and supination, substituting for those gross motions a rotation by twirling between the fingers, preferably the thumb and forefinger. The rotation of the invention is the only motion needed for one suture.

The invention includes two main pieces, a palm piece which rests immobile against the palm of the hand, and a finger piece which is fixed to the palm piece by a bearing so that it can rotate about the bearing axis, which extends outwardly from the palm piece. The thumb and fingers twirl the finger piece about the bearing axis by moving skew to the axis while in contact with the barrel of the finger piece.

At the end of the finger piece, opposite the rotatable coupling to the palm piece, is a needle clutch which can grip the needle for suturing and release it for re-positioning.

Suturing needles are bent to a circular shape and ideally the track of the needle through the sutured flesh is of just that shape to minimize trauma. The present invention preferably offsets the needle clutch from the bearing axis so that the rear end of the needle, which is gripped in the clutch, describes a small arc as the finger piece is twirled. The offset of the clutch from the axis is preferably made equal to the radius of the curved needle itself; then, when the needle is gripped in the clutch so that the arc of the needle's bend is centered on the twirling axis, the needle will follow its own arc as the finger piece is twirled. That is, the curved body of the needle will follow in the path of the pointed tip, and no part of the needle will leave the circular path swept out by the needle point.

The surgeon can position the needle point at the site where the suture is to start, and then twirl the finger piece; this simple motion will automatically move the needle point into and then out of the tissue, trailing the suture behind, to complete the stitch in one twirl with both speed and accuracy. No gross hand or arm motion is required.

Twirling does not use large forearm muscles and does not throw off the tip of a held object. This is easily demonstrated by holding a pen or pencil tip at a point near a surface and twirling it. The tip wobble is less than with pronation and supination, especially when the end of the implement is short and is held loosely against the palm.

An additional improvement of finger twirling over wrist rotation is that the surface of the forearm is less disturbed by the motion, so that resting the forearm against a support to stabilize it is less likely to throw the needle off track. This is also easily shown by loosely holding the operating forearm encircled with the other hand while first rotating the wrist and second making twirling motions with the thumb; it will be found that much larger motions are felt during pronation and supination than during twirling. Not only are the twirling muscles smaller, but they are also deeper.

It can also be noted that the ulna bone of the forearm, which normally is rested on a surface such as a table to stabilize it, does not move at all during twirling, and there are no muscles between the ulna and the support which can jostle the bone. Of course, when the wrist rotates this bone moves side-to-side and jostles the hand.

While the needle clutch may be operable to grasp and release the needle by any sort of control or device, preferably the needle clutch grips the needle by a retraction of the finger piece toward the palm piece. The present invention uses the finer muscles of the inner forearm to grip and release the needle, just as it uses these muscles to twirl the needle.

To provide for this capacity the finger piece includes two parts, a sleeve and a stylet (or rod) inserted in the sleeve for telescoping motion. Preferably, the axis of rotation of the finger piece is coaxial with the bearing axis, the stylet (and the bore of the sleeve in which it moves), and also the outside finger-grip surface where the twirling fingers rest. The needle clutch jaws are at the tips of the sleeve and the stylet, respectively, with the sleeve jaw preferably on the inside of an L-shape or J-shaped tip, facing the stylet tip, so that needle is gripped when the sleeve is retracted or drawn in toward the palm piece, while the stylet remains at the same distance from the palm piece.

The stylet is preferably fastened to the bearing which couples the finger piece to the palm piece. The stylet is able to rotate, but not translate, relative to the palm piece. Conversely, the sleeve should not rotate relative to the stylet, only translate axially, so that the jaws remain aligned in the axial direction and the needle will not roll between the jaws. The stylet and sleeve are made irrotational by a pin and slot arrangement, mating splines, or the like.

The needle is held by drawing the fingers slightly backward relative to the palm, which causes the sleeve jaw to clamp against the stylet jaw, gripping the needle between them. The fingers are relaxed away from the palm to release the needle.

As with twirling, the motions of gripping and releasing the needle cause no erratic motion of the clutch tip. The finger motions are fine and do not disturb the angle or the position of the tip. Hand anatomy permits the pursed fingers to be drawn in toward the palm without generating other motions.

Preferably, no leverage is used in the invention: the holding force is directly applied. This reduces the total motion of the hand and also tends to reduce unwanted motions. Direct force is sufficient for suturing and no springs are required to bias the jaws closed, although such a spring may be present, if one wanted to create such a bias.

The palm piece may be symmetrical like a doorknob, but preferably is specially shaped for either a right hand or a left hand. Preferably, it includes indentations where the fourth and fifth fingers (pinky and ring fingers) can rest.

The invention is easily adapted to different shapes for specific operations and individual surgeons. However, with a rigid stylet and sleeve there can be no substantial lateral offset of the finger piece and the needle clutch. In certain operations such an offset is desirable, and a second embodiment of the invention provides this offset.

In the alternate embodiment, the sleeve is laterally bendable but stiff against torsion, and runs over the stylet for some distance where the stylet is curved. The stylet is rigid, so that as the sleeve is twirled by the fingers at one end away from the tip, the other end of the sleeve which is close to the tip twirls with it. In this embodiment the stylet does not rotate relative to the palm piece; instead it is rigidly fixed there, but the stylet includes a bearing at the other end which permits the stylet jaw of the needle clutch to revolve. The sleeve jaw is simply fixed at the end of the sleeve, as in the first embodiment.

The alternate embodiment permits the suturing operation to be offset from the line extending from the palm piece along the grasped portion of the finger piece. This line is no longer the axis of rotation of the needle clutch; that rotation axis is offset from the straight portion of the stylet (if any). This provides additional flexibility in suturing in hard-to-reach positions because the surgeon's hand can be positioned in any orientation relative to the arc of suturing.

BRIEF DESCRIPTION OF THE DRAWING

The above and other objects and the nature and advantages of the present invention will become more apparent from the following detailed description of an embodiment[s] taken in conjunction with drawings, wherein.

DETAILED DESCRIPTION OF THE PREFERRED EMBODIMENTS

Figure 1:
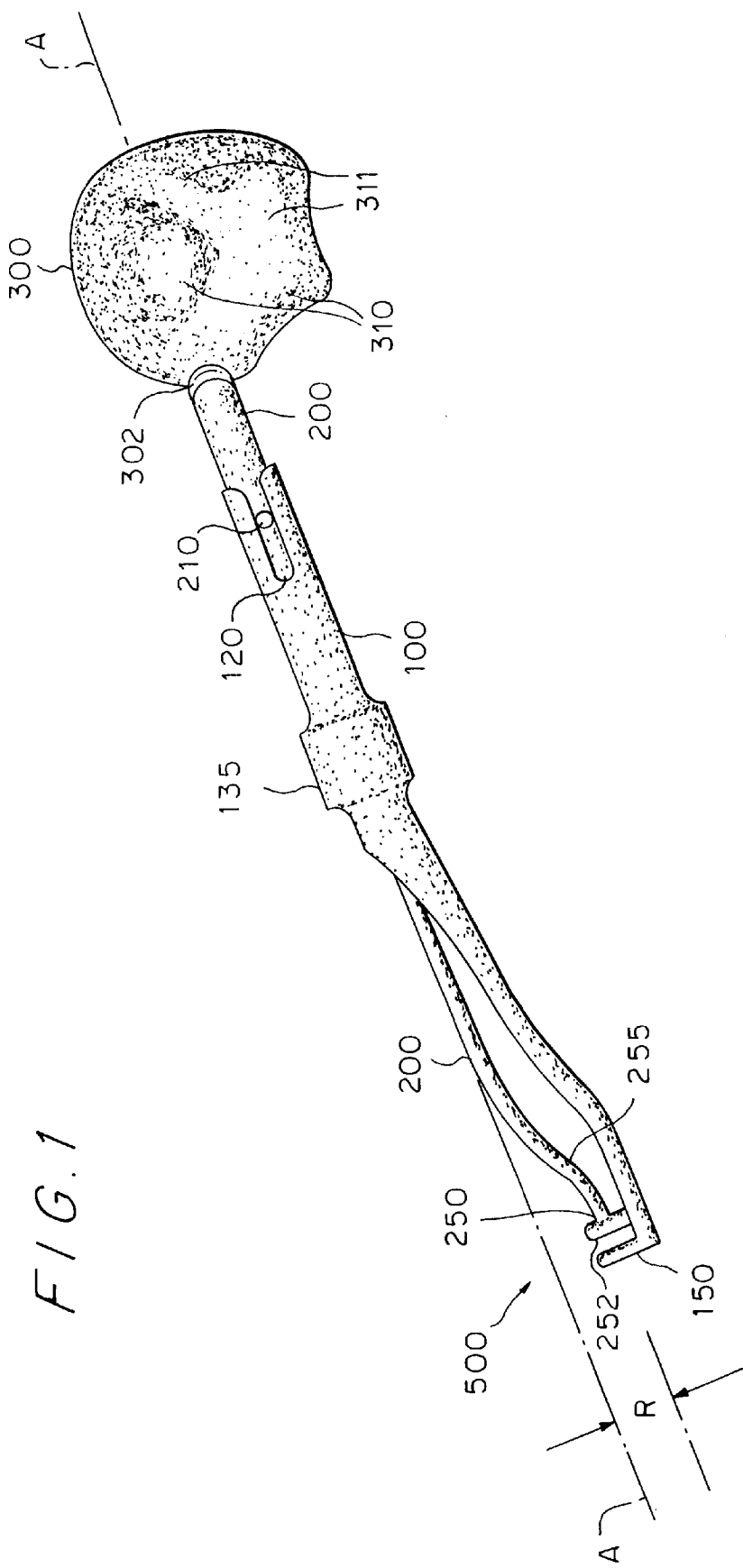
FIG. 1 is a perspective view of the first preferred embodiment of the invention.

FIG. 1, which shows the present invention in a first preferred embodiment, includes a finger piece further comprising a stylet 200 and a sleeve 100, and a palm piece 300. The palm piece 300 and the stylet 200 are optionally coupled by a bearing 302 which permits them relative motion about a bearing axis A, but preferably no other relative motion. The two parts of the finger piece, the stylet 200 and sleeve 100, are relatively slidable along the axis A; the slidable motion may be provided by telescopic sliding of a cylindrical portion of the stylet 200 within a bore in the sleeve 100.

Relative rotation may be prevented by a pin 210 on the stylet 200 and a slot 120 in the sleeve 100, in which the pin 210 slides. Thus, the sleeve 100 can both rotate about and slide along the axis A relative to the palm piece 300.

The sleeve 100 includes a finger barrel or grip portion 135 which is grasped between the thumb and fingers during use. It may be knurled or made of high-friction material. However, the grip portion of the sleeve 100 may be any portion on which the fingers fall when the needle holder is grasped, and the present invention does not require any protruding or otherwise distinguishable feature; it only requires that there be some portion of the sleeve 100 which can be gripped by the fingers, and such a portion is defined here and in the following claims as a "grip portion".

The stylet 200 extends away from the palm piece 300 (downward and to the left in FIG. 1), bends in a portion 255, and terminates in a stylet jaw 250. The jaw 250 includes a gripping surface 252 facing away from the palm piece 300 and toward a sleeve jaw 150. The two jaws 150, 250 are shaped to hold a suturing needle between them. The area where the needle N is gripped is denoted as the needle clutch 500.

Figure 2:
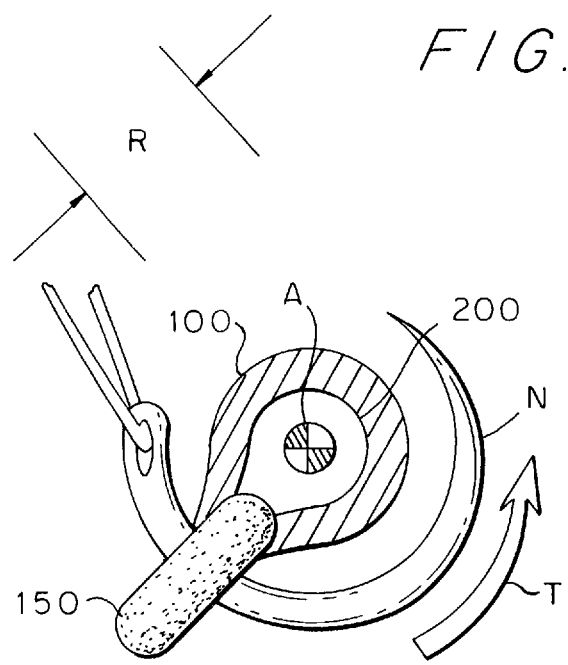
FIG. 2 is a schematic view, partially in cross-section, looking along an axis of rotation.

FIG. 2 shows the needle N held between the jaws, as seen along the axis A (indicated by a centerline mark in FIG. 2). The needle N is not seen in FIG. 1. The needle N can be gripped by the surgeon retracting his or her fingers toward the palm of the hand, moving the barrel or grip portion 135 axially toward the palm piece 300; this closes the jaws 150, 250 together to hold the needle N.

FIGS. 1 and 2 show the offset R of the axis A from the point at which the needle N is clutched. The needle N is preferably bent into substantially an arc of a circle, as is conventional with suturing needles, and is held so that its arc is centered on the axis A; this is shown in FIG. 2. The jaws 150, 250 can include shapes, such as grooves (not shown) to align the needle to the proper arc.

Figure 3:
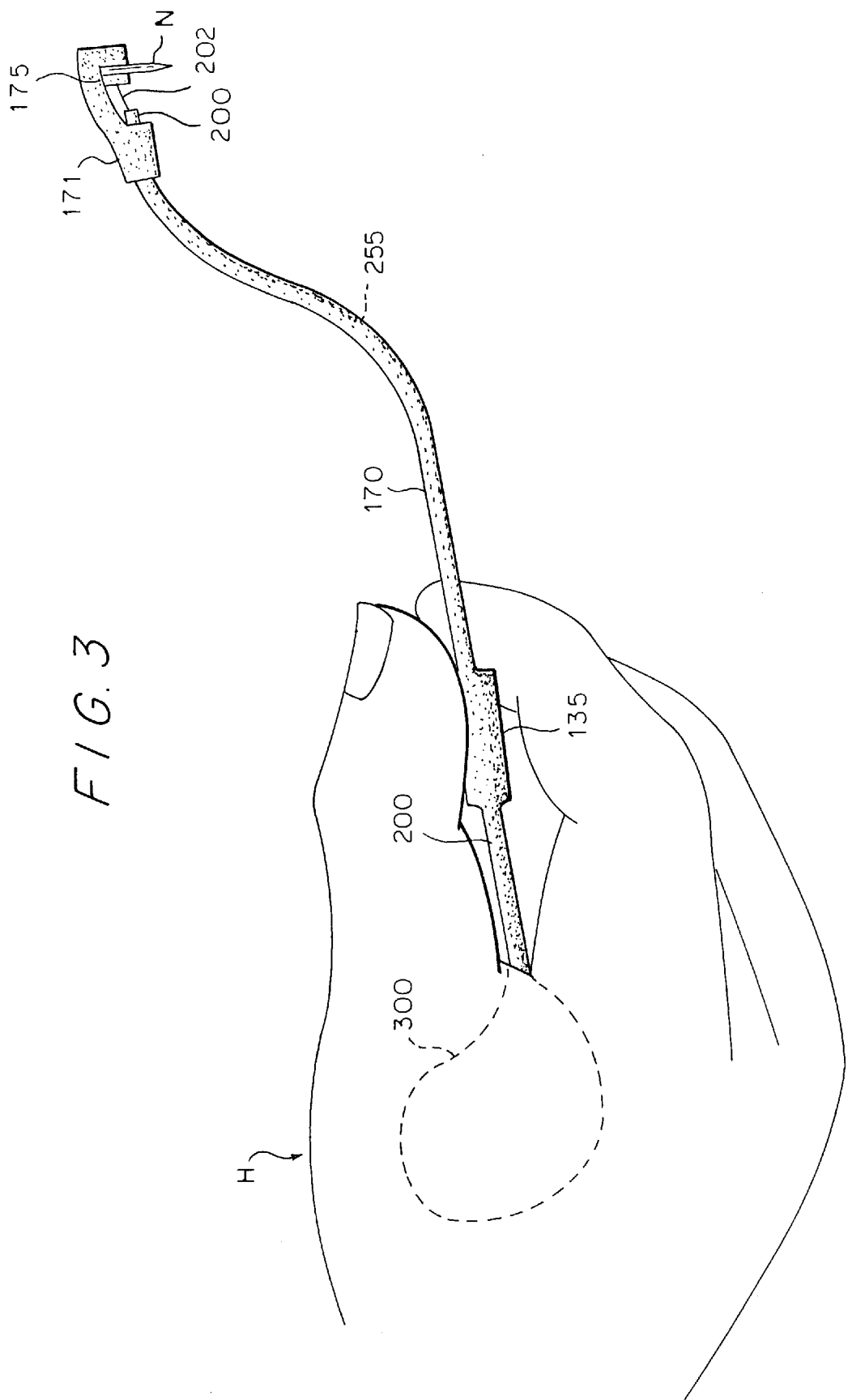
FIG. 3 is a perspective view of the second preferred embodiment of the invention.

While the needle N is gripped in the position of FIG. 2 by the retraction of the surgeon's fingers on the barrel grip 135, the entire finger piece 100, 200 can be twirled by the surgeon twisting her or his fingers to rotate the barrel 135. This will cause the needle N to swing about the axis A in the direction of the arrow T in FIG. 2, so that the needle follows along the arc traced out by the sharp point of the needle N. The needle N can be moved in a semi-circular path of radius R through flesh to be sutured simply by twirling the fingers. The finger position for twirling is shown in FIG. 3. Then the needle N is released by extending the fingers to push the barrel 135 away from the palm piece 300. The needle may then be regripped near the point thereof by the needle holder to complete the suture.

Palm piece 300 includes impressions 310 to accommodate the fourth digit for a right-handed surgeon and impressions 311 for accommodating the fifth digit of a right-handed surgeon. For a left-handed surgeon the palm piece 300 would be a mirror image of that shown. Various sizes and patterns are possible in the invention.

The bearing 302 may include a simple bore, especially if the palm piece 300 is molded of relatively slippery plastic such as nylon; a sleeve of similar material, for example TEFLON; roller or ball bearings; and any other conventional bearing arrangement, which preferably is sterilizable and/or disposable for antisepsis. Preferably, the stylet 200 is releasably held in the palm piece 300 by a snap fit, screw thread, or some other conventional means (not shown). If the stylet 200 does not disassemble from the palm piece 300, then the non-cylindrical portion of the stylet 200 is shaped so that the entire stylet 100 can be withdrawn from the sleeve 100 in the direction of jaw separation.

FIG. 3 shows a second preferred embodiment of the present invention held by a surgeon's hand H. Analogous elements are denoted by the same reference numbers as in the other figures. The palm piece 300 is shown in phantom view. Unlike the embodiment of FIG. 1, there is no bearing 302: the stylet 200 is rigidly (or demountably) attached to the palm piece 300 so that the stylet 200 cannot easily swing about the line coaxial with the initial straight portion of the stylet 200 adjacent the palm piece 300. The stylet 200 also includes a bent or curved portion 255, clearly shown in FIG. 3.

Disposed along the straight portion is the barrel or grip 135. As in the first embodiment, twirling the grip 135 also twirls the needle N; however, there is no rigid sleeve 100 as in the embodiment of FIG. 1, but rather a tube 170 which resists torque but permits bending. The tube 170 has been slid over the stylet 200. When the grip 135 is twirled, the clutch end of the tube 170 also turns, while the tube 170 otherwise remains in place over the curved stylet 200; when the grip 135 is pushed or pulled, the tube 170 slides snake-like along the stylet 200. In the following claims, "telescopic" covers motions such as those possible in this embodiment.

Figure 4:
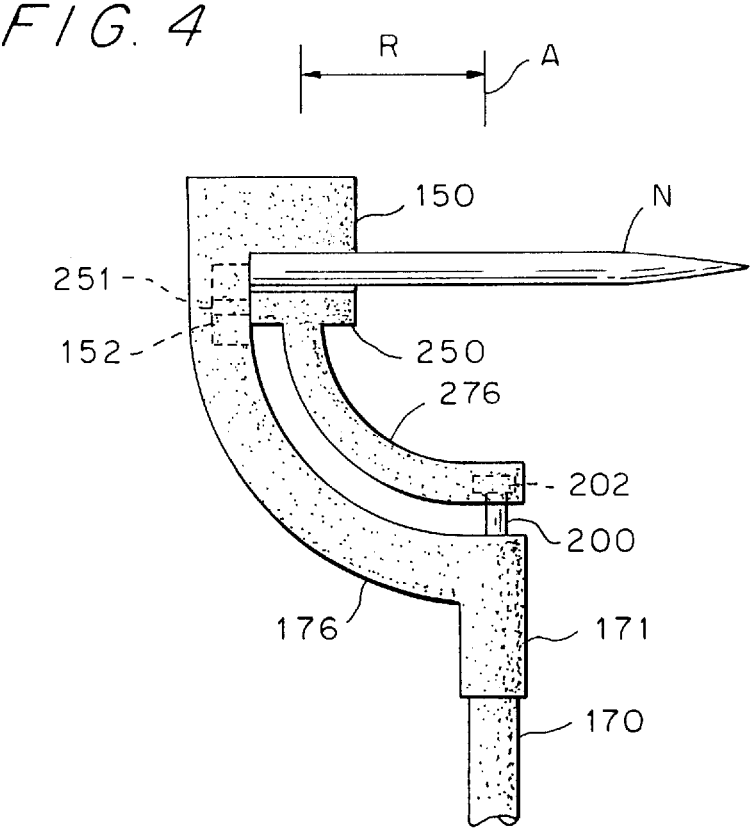
FIG. 4 is a detailed view of the tip of the needle holder of FIG. 3.

The needle-clutching mechanism is also shown in FIG. 4 in greater detail. The entire assembly shown in FIG. 4 rotates about the axis A, except for the small portion of the rigid stylet 200 which is visible between the curved arms 176 and 276. Arm 276, at the end of which is the stylet jaw 250, rotates about a bearing 202 on the end of the stylet 200. A small pin 251 at the end of the arm 276 engages a slot 152 in the arm 176. The arm 176 is fixed at the end of the tube 170. Thus, when the surgeon twirls the grip 135 the arm 276 revolves about the axis A, and the needle N is carried in its arc as in FIG. 2. Needle N is clutched between jaws 150 and 250 by retracting the grip 135 (FIG. 3).

The present invention is not limited to needles as illustrated above, but relates to any sort of surgical fastener which can be passed through flesh in a generally arcuate path. Thus, the invention in the preferred embodiments can also be used with a plurality of arcuate staples which are left in place, rather than with a single needle that is pulled through after insertion to leave a thread behind. Such a staple might lack an eye hole. It could be closed by plastic deformation after it were passed through the flesh to be stapled. In the following claims, "needle" includes any rigid arcuate object adapted to be passed through flesh in surgery.

The present invention encompasses several additional embodiments.

Figure 5:
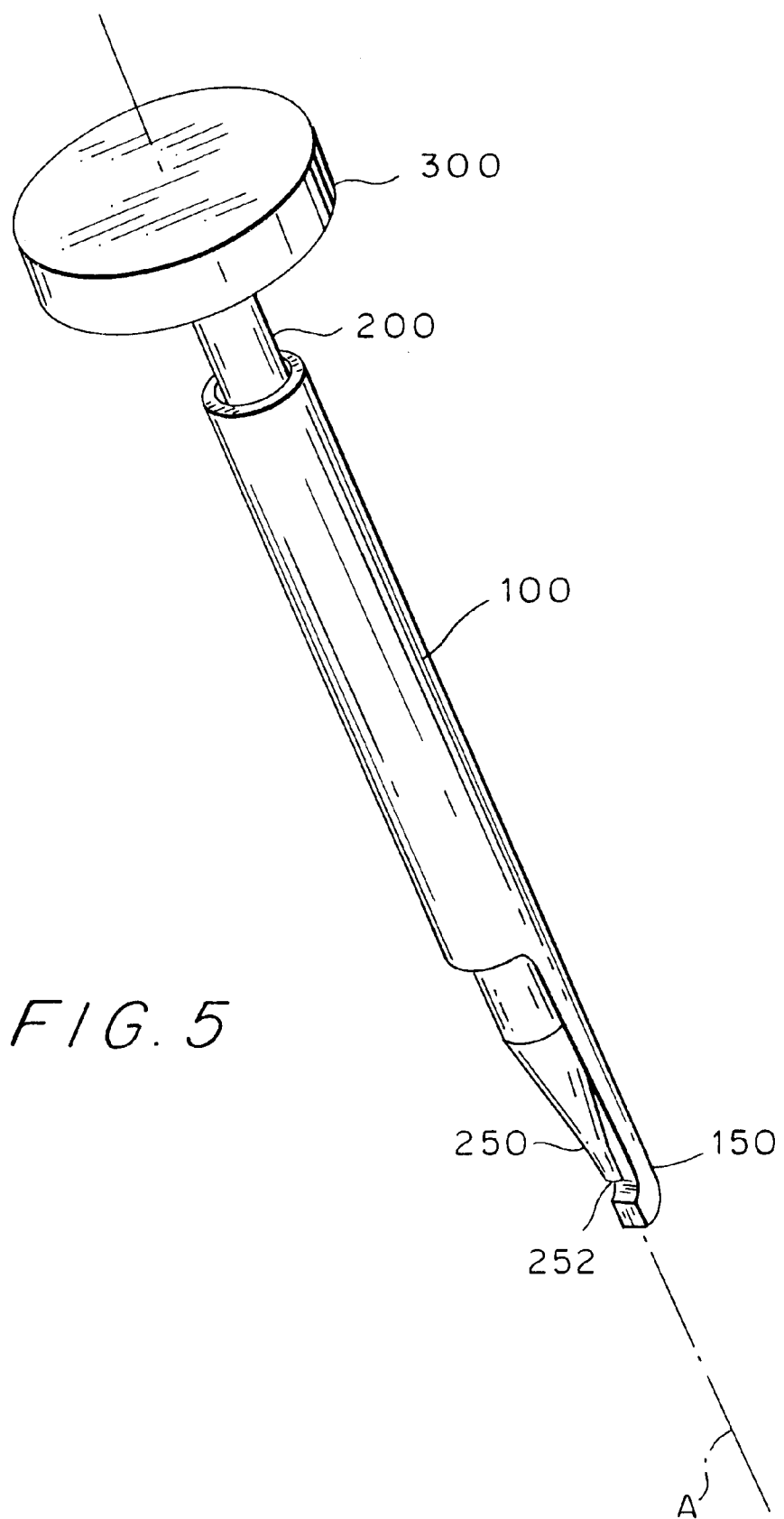
FIG. 5 is a perspective view of a third embodiment of the invention.

FIG. 5 shows an embodiment which lacks the curve 255. The axis A passes directly through the faces of the jaws 150, 250. The distance R is negligible. The palm piece 300, which may be shaped as illustrated or as the palm pieces of the previously described embodiments, is non-rotatably connected to the spline 200. There is no need for the spline 200 to swivel with respect to the palm piece 300 in this simplest embodiment. Furthermore, the sleeve 100 is free to rotate about the spline 200 so as to rotate the effective opening of the jaw 250 by means of the surgeon simply rotating the sleeve 100 about the spline 200 with his fingers. The closing of the jaw 250, and thus gripping of the needle when in use, is still accomplished by the surgeon retracting his or her fingers toward the palm of the hand, moving the sleeve 100 and, thus, the sleeve jaw 150 toward the palm piece 300. Because of the convenient ergonomic construction, the jaw may be opened, closed and rotated by simple finger movements of the surgeon without the need of spring biasing elements.

One alternative embodiment of the invention (not shown) includes an automatic or semi-automatic mechanism to revolve the needle N about the axis A. The mechanism might cause the needle to move through its arc whenever an electric finger switch is pressed, for example. Rapid semi-automatic twirling could also be realized with a wind-up spring enclosed in the palm piece 300, triggered by a release button. This could be useful in certain operations because a high-speed penetration of the needle which could be achieved with powered twirling. This would decrease the deformation of the flesh under the pressure of the needle point and make for more accurate placement of the sutures. Even a small volume of flesh has an appreciable inertia force when accelerated rapidly.

In addition, rapid twirling might help the surgeon compensate for motion of the tissue being sutured, since the needle holder would only need to be maintained in position for a brief time.

Another variation is that the needle clutch could be operated by some other mechanism activated by compressing the or extending them away. Needle clutching and release could also be accomplished by any sort of conventional mechanism such as a solenoid controlled by a switch on the sleeve, and so on.

The present invention encompasses a device pulling a flexible fastener (e.g., suturing thread) through an arcuate path and leaving the flexible fastener behind, even if no needle separate or separable from the device of the invention is provided or used. A needle may be incorporated as a non-separating part of the invention in combination with a shuttle, in the manner of a sewing machine.

The invention in general includes any means for holding a fastener, whether needle or staple, in a clutch and simultaneously rotating the clutch about an axis of rotation (A) at a distance from the axis substantially equal to the radius. Such a means includes all the embodiments discussed above and others within the scope of the following claims.

The industrial applicability is in medical operations. The problem solved by the invention is lack of control in suturing.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A twirlable needle holder for suturing with a needle (N), the needle holder being operable by a hand having a palm and fingers, the needle holder comprising;
   a palm piece (300); and
   a finger piece (100,200) rotatably coupled to the palm piece to rotate about a twirling axis (A), the finger piece further comprising
      a grip portion (135) for twirling the finger piece about the axis, and
      a needle clutch (500) disposed generally at an end of the finger piece opposite the palm piece, the needle clutch being operable by the hand to grasp and release the needle by motion of the grip portion parallel to the twirling axis.

2. The needle holder according to claim 1, wherein the needle clutch is offset from the axis.

3. The needle holder according to claim 2, wherein the needle clutch is offset from the axis by a distance (R), whereby
   if the needle intended to be held when in use includes a portion shaped substantially as an arc, then the distance (R) is substantially equal to a radius of the arc.

4. A twirlable needle holder for suturing with a needle (N), the needle holder being operable by a hand having a palm and fingers, the needle holder comprising;
   a palm piece (300); and
   a finger piece (100,200) rotatable coupled to the palm piece to rotate about a twirling axis (A), the finger piece further comprising
      a grip portion (135) for twirling the finger piece about the axis, and
      a needle clutch (500) disposed generally at an end of the finger piece opposite the palm piece, the needle clutch being operable by the hand to grasp and release the needle;
   wherein the finger piece further comprises a stylet and a sleeve axially surrounding said stylet, and the needle clutch includes opposing jaws, the opposing jaws including a stylet jaw (252) connected to said stylet and a sleeve jaw (150) connected to said sleeve.

5. The needle holder according to claim 4, wherein the needle clutch is operable to grasp and release the needle by a motion of said sleeve about said stylet generally along the axis, so as to open and close said needle clutch.

6. The needle holder according to claim 4, wherein the stylet is coupled to the palm piece by a bearing (302).

7. The needle holder according to claim 6, wherein the stylet and the sleeve are telescopically slidable and the stylet jaw and the sleeve jaw are relatively movable by telescopic motion of the sleeve along the stylet.

8. The needle holder according to claim 7, including means (120, 210) to prevent the stylet and the sleeve from rotating relative to one another about the axis.

9. The needle holder according to claim 5, wherein the stylet and the sleeve are relatively rotatable, the stylet is irrotatable relative to the palm piece, and the sleeve comprises a bendable tube (170).

10. The needle holder according to claim 9, wherein the stylet is coupled by a bearing (202) to an arm (276) of the stylet jaw, and the stylet jaw is slidably coupled to the sleeve jaw (251, 152).

11. The needle holder according to claim 9, wherein the stylet includes a curved portion (255).

12. A device to be used by a user having fingers, for suturing with a fastener of the type including a portion shaped substantially as an arc, comprising:
   means for holding the fastener in a clutch and simultaneously rotating the clutch about an axis of rotation (A) at a distance from the axis substantially equal to the radius;
   wherein the means for holding the fastener in the clutch further comprises a finger grip; and
   wherein the means for rotating the clutch further comprises means for twirling by the fingers.

13. A needle holder for suturing with a needle (N), the needle holder being operable by a hand having a palm and fingers, the needle holder comprising:
   a palm piece (300);
   a stylet (200) connected to said palm piece, said stylet having a jaw surface (252) at the tip thereof opposite said palm piece; and a sleeve (100) disposed about said stylet (200), said sleeve being rotatable with respect to said palm piece and said sleeve terminating in a jaw surface (150) which is disposed opposite and in operable conjunction with said stylet jaw surface (252);

wherein said jaw surfaces may be opened and closed when in use, with said palm piece being held against the palm of the operator, by the operator gripping said sleeve with his or her fingers and moving said sleeve with respect to said stylet by extending and retracting the fingers.

* * * * *